United States Patent
De La Torre et al.

(10) Patent No.: US 7,381,750 B2
(45) Date of Patent: Jun. 3, 2008

(54) AMINO-PHENOXYMETHYL-BENZAMIDE OPIOID RECEPTOR ANTAGONISTS

(75) Inventors: Marta Garcia De La Torre, Madrid (ES); Charles Howard Mitch, Columbus, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/598,696

(22) PCT Filed: Mar. 8, 2005

(86) PCT No.: PCT/US2005/007051

§ 371 (c)(1),
(2), (4) Date: Jun. 6, 2007

(87) PCT Pub. No.: WO2005/090286

PCT Pub. Date: Sep. 29, 2005

(65) Prior Publication Data

US 2007/0287751 A1    Dec. 13, 2007

(30) Foreign Application Priority Data

Mar. 12, 2004 (EP) .................................. 04380058

(51) Int. Cl.
*A61K 31/085* (2006.01)

(52) U.S. Cl. ...................................... 514/620; 564/165

(58) Field of Classification Search ................ 514/471, 514/620; 564/165
See application file for complete search history.

(56) References Cited

U.S. PATENT DOCUMENTS

| 5,965,741 A | 10/1999 | Breault et al. | |
|---|---|---|---|
| 6,410,561 B1 * | 6/2002 | Shinkai et al. ............... | 514/313 |

FOREIGN PATENT DOCUMENTS

| GB | 1 504 604 | 3/1978 |
|---|---|---|
| WO | WO 02/078693 | 10/2002 |
| WO | WO 2004/026305 | 4/2004 |
| WO | WO 2004/080996 | 9/2004 |
| WO | WO 2004/090968 | 9/2004 |
| WO | WO 2005/061442 | 7/2005 |
| WO | WO 2005/066164 | 7/2005 |

OTHER PUBLICATIONS

West, Anthony R., Solid State Chemistry and its Applications, Wiley, New York, 1988, pp. 358 & 365.*
J. Med. Chem, vol. 27, No. 2, pp. 129-143 (1984).

* cited by examiner

*Primary Examiner*—Rita Desai
*Assistant Examiner*—David K O'Dell
(74) *Attorney, Agent, or Firm*—John C. Demeter; Francis O. Ginah

(57) ABSTRACT

A compound of the formula (I) wherein the variables X1, X2, $R^1$ to $R^7$ including $R^{3'}$, j, k, p, y, and z, are as defined or a pharmaceutically acceptable salt, solvate, enantiomer, racemate, diastereomer or mixtures thereof, useful for the treatment, prevention or amelioration of obesity and Related Diseases is disclosed.

3 Claims, No Drawings

AMINO-PHENOXYMETHYL-BENZAMIDE OPIOID RECEPTOR ANTAGONISTS

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, certain antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed phenylpiperidine opioid antagonists useful for the treatment of diabetes and obesity. In particular, U.S. Pat. No. 4,891,379 disclosed the compound LY 255582 represented by the structure

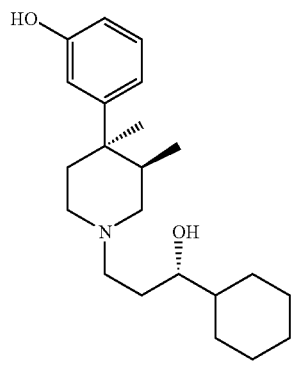

U.S. Pat. No. 4,191,771 also disclosed compounds useful as opioid antagonists. Also, bicyclic analogs of phenyl piperidine have been prepared and reported as opioid antagonists in Wentland, et al., Biorganic and Medicinal Chemistry Letters 11 (2001) 623-626; see also Wentland, et al., Bioorganic and Medicinal Chemistry Letters 11 (2001) 1717-1721. Finally, European Patent application number EP 1 072592A2 filed May 18, 2000, discloses phenylpiperidine compounds of formula 1

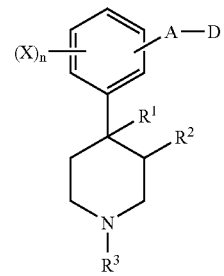

wherein A, D, $R^1$, $R^2$, $R^3$, X, and n have meanings given in the description, which are useful in the prophylaxis and in the treatment of diseases mediated by opioid receptors such as pruritus.

U.S. Pat. No. 6,140,352 discloses the compound of formula

Formula 1

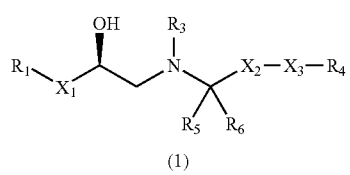

wherein the variables $X_1$, $X_2$, $X_3$ $R_1$, $R_3$, $R_4$, $R_5$ and $R_6$ are as described therein, as agonists of the beta adrenergic receptor useful for the treatment of diabetes and obesity.

PCT application WO 9215304 discloses the compounds of formula I

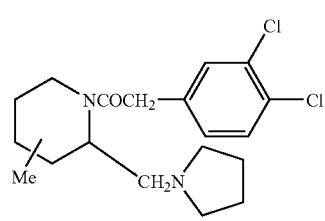

Compound 1 above, encompasses azacyclic and heterocyclic compounds for treatment of cerebral ischemia.

Regardless of these and other disclosures of compounds useful as opioid receptor antagonists, or useful for the treatment of obesity, and/or diabetes by other mechanisms, or having structures partially close to the compounds of the present invention there remains an unmet medical need for useful, safe, effective and/or alternate treatments or prophylaxis of diseases associated with opioid receptors, particularly obesity and Related Diseases.

SUMMARY OF THE INVENTION

The present invention provides a compound of the formula (I)

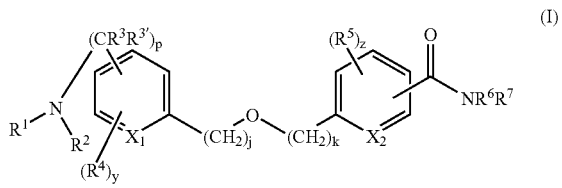

p is 0, 1, or 2;

y is 0, 1, or 2; and z is 0, 1, or 2;

j and k are each independently 0, 1, or 2 provided that j and k are not simultaneously equal to 0;

$X_1$ and $X_2$ are each independently is CH, or N;

$R^1$ and $R^2$ are independently selected from hydrogen, $C_1$-$C_8$ alkyl, $C_2$-$C_8$ alkenyl, $C_2$-$C_8$ alkynyl, phenyl, $C_1$-$C_{10}$ alkylaryl, $SO_2R^8$, $(CH_2)_nC(O)NR^8R^8$, $SO_2C_1$-$C_{10}$ alkylaryl, $SO_2C_1$-$C_9$ alkylheterocyclic, $C_4$-$C_{10}$ alkylcycloalkane, $(CH_2)_nC(O)OR^8$, and $(CH_2)_nC(O)R^8$; wherein each of the alkyl, alkenyl, and aryl groups are optionally substituted with one to two groups independently selected from $C_1$-$C_8$ alkyl, $C_2$-$C_8$ alkenyl, phenyl, $C_3$-$C_8$ cycloalkyl, $C_1$-$C_8$ alkylaryl, and $C(O)C_1$-$C_8$ alkyl; and wherein $R^1$ and $R^2$ may optionally combine with each other to form a 4, 5, 6, or 7-membered nitrogen-containing heterocycle which nitrogen-containing heterocycle may further have substituents selected from the group consisting of oxo, amino, $C_1$-$C_8$ alkyl, $C_2$-$C_8$ alkenyl, $C_2$-$C_8$ alkynyl, phenyl, $C_1$-$C_3$ alkylaryl, $C(O)C_1$-$C_8$ alkyl, $CO(O)C_1$-$C_8$ alkyl, halo, $C_1$-$C_3$ haloalkyl;

$R^3$ and $R^{3'}$ are each independently selected from hydrogen, $C_1$-$C_8$ alkyl, $C_2$-$C_8$ alkenyl, $C_2$-$C_8$ alkynyl, phenyl, aryl, $C_1$-$C_8$ alkylcycloalkyl, and $C_1$-$C_8$ alkylaryl;

$R^4$ and $R^5$ are each independently selected from hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_mNSO_2C_1$-$C_8$ alkyl, $(CH_2)_nNSO_2$phenyl, $(CH_2)_mNSO_2$aryl, —$C(O)C_1$-$C_8$ alkyl, and —$C(O)OC_1$-$C_8$ alkyl; wherein each $R^4$ and $R^5$ is attached to its respective ring only at carbon atoms; wherein m is 1 or 2; and n is 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, $C(O)C_1$-$C_8$ alkyl, $SO_2C_1$-$C_8$ alkyl, $SO_2C_1$-$C_8$ alkylaryl, $SO_2C_1$-$C_8$ alkylheterocyclic, aryl, $C_1$-$C_8$ alkylaryl, $C_3$-$C_7$ cycloalkane, $C_1$-$C_6$ alkylcycloalkane, $(CH_2)_mC(O)OR^8$, $(CH_2)_mC(O)NR^8R^8$, $(CH_2)_mC(O)NR^8R^8$, and $(CH_2)_mNSO_2R^8$; wherein each of the alkyl, alkenyl, and aryl groups are optionally substituted with one to two groups independently selected from $C_1$-$C_8$ alkyl, $C_2$-$C_8$ alkenyl, phenyl, and $C_1$-$C_8$ alkylaryl; and wherein $R^6$ and $R^7$ may independently combine with each other, and with the nitrogen atom to which they are attached to form a 4, 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, and $C_1$-$C_8$ alkylaryl;

$R^8$ is independently selected from hydrogen, $C_1$-$C_8$ alkyl, $C_2$-$C_8$ alkenyl, phenyl, benzyl, and $C_5$-$C_8$ alkylaryl; or a pharmaceutically acceptable salt, solvate, prodrug, enantiomer, racemate, diastereomer, or mixture of diastereomers thereof.

The present invention also provides a method for the prevention, treatment and/or amelioration of the symptoms of obesity and Related Diseases comprising administering a therapeutically effective amount of a compound of formula (I) or a pharmaceutically acceptable salt, solvate, enantiomer, racemate, diastereomer or mixture of diastereomers thereof.

The present invention also provides a pharmaceutical formulation comprising a compound of formula I in association with a carrier, diluent and/or excipient.

The present invention also relates to a method for the treatment and/or prophylaxis of obesity and Related Diseases including eating disorders (bulimia, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperlipoproteinemia, substance abuse, drug overdose, compulsive behavior disorders (such as paw licking in dog), and addictive behaviors such as for example, gambling, and alcoholism, comprising administering a therapeutically effective amount of a compound of formula I or a pharmaceutically acceptable salt, solvate, enantiomer, racemate, diastereomer or mixture of diastereomers thereof.

The present invention relates to a compound of formula (I) useful for the manufacture of a medicament for the treatment, prevention and/or amelioration of symptoms associated with obesity and Related Diseases.

In another embodiment, the present invention relates to a compound of formula I or a pharmaceutically acceptable salt, solvate, enantiomer, racemate, diastereomer or mixture thereof, useful as an appetite suppressant.

The present invention relates to a method of achieving weight loss while maintaining lean muscle mass or minimizing the loss of lean muscle mass comprising administering a compound of formula I or a pharmaceutically acceptable salt, solvate, enantiomer, racemate, diastereomer or mixture thereof, to a patient in need thereof.

The present invention provides a compound of formula I useful singly or in combination with other agents approved for the treatment, prevention and/or amelioration of obesity and related diseases and symptoms thereof.

DETAILED DESCRIPTION OF THE INVENTION

As used herein, the term "patient" includes human and non-human animals such as companion animals (dogs and cats and the like) and livestock animals.

The preferred patient of treatment, amelioration and/or prevention of obesity and Related Diseases is a human.

The terms "treating" and "treat", as used herein, include their generally accepted meanings e.g. preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of obesity and Related Diseases and the symptoms associated therewith, in a patient afflicted with same or reducing the likelihood that the recipient of a compound of formula I will be afflicted with or develop any of the pathological conditions or sequela thereof described herein.

As used herein, the term "effective amount" is synonymous with "effective dose" and means an amount of a compound of formula I that is sufficient in one or more administrations for preventing, ameliorating or treating a condition, or detrimental effects thereof, herein described, or an amount of a compound of formula I that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or a combination of a compounds of formula I or a combination of a compound of formula I and a co-antagonist of the opioid receptor or a combination a compound of formula I and other effective anti-obesity, weight loss or antidiabetic agent.

The term "formulation", as in pharmaceutical formulation, or "pharmaceutical composition" is intended to encompass a product comprising the Active Ingredient (as defined supra), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompass a compound of the formula I and a pharmaceutically acceptable co-antagonist of opioid receptors useful for the treatment and/or prevention of obesity or Related Diseases.

The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression (particularly that induced by the awareness and loss of self esteem associated with obesity), anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinemia.

As used herein "other agents" approved for the treatment of obesity and/or related disease, or useful for weight loss and/or appetite suppression include but are not limited to Xenical®, Meridia®, Lipitor®, Crestor®, Pravachol®, Zetia®, cannabinoid receptor antagonists, and other opioid receptor antagonists.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a monocycle which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1, 2 or 3 double bonds. A nitrogen containing heterocycle may be attached to or fused to an existing ring substituent thus forming a bicyclic or tricylic ring system. Nonetheless, the direct result of the formation of a nitrogen containing heterocycle by the joining of two groups and the nitrogen atom to which they are attached is to form a monocycle.

The term "$C_1$-$C_8$ alkyl" or $C_{1-8}$ alkyl" refers to and includes all groups, structural isomers and/or homologues of alkyl groups having from 1 to 8 carbon atoms. When the term $C_1$-$C_8$ alkyl precedes or prefixes another group, the term $C_1$-$C_8$ alkyl, only limits the number of carbon atoms in the alkyl component. For example $C_1$-$C_8$ alkyaryl means an aryl group having a $C_1$-$C_8$ alkyl group substituent such that the number of carbon atoms in the group $C_1$-$C_8$ alkylaryl is effectively the number of carbon atoms in the aryl group plus the number of carbon atoms in the $C_1$-$C_8$ alkyl group. Similarly, the term "$C_1$-$C_8$ alkylcycloalkyl" refers to a cycloalkane group having a $C_1$-$C_8$ alkyl substituent, and wherein the entire group $C_1$-$C_8$ alkylcycloalkane may itself be a substituent attached at either the alkyl group or the cycloalkyl group to a substrate. The definition and usage applies equally to other homologues of $C_1$-$C_8$ such as for example, $C_1$-$C_7$, $C_1$-$C_6$ etc.

The term "cycloalkane" or "cycloalkyl" means cycloalkanes having from 3 to 8 carbon atoms i.e. from cyclopropane to cyclooctane.

The term "hal" or "halo" as used herein refers to a halogen including fluorine, chlorine, bromine or iodine.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as defined previously.

The term "aryl" as used herein refers to compounds or groups having the Huckel 4n+2 pi electron arrangement and includes phenyl, benzyl, naphthyl, but excludes carbazoles and other fused tricyclic ring structures.

It is understood by one of skill in the art that where a substituent is absent, a hydrogen atom is indicated to achieve the required valency unless otherwise indicated. For example, if y is 0, then $R^4$ is absent, and all applicable positions on the ring have hydrogen atoms to achieve the required valency for atoms in the ring.

As used herein, the term "protecting group" refers to a groups useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, $3^{rd}$ edition, Greene, T. W.; Wuts, P.G.M. Eds.; John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, maleate, mandelate, mesylate, methylbromide, methylnitrate, methylsulfate, sulfite, sulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

A compound of the invention as illustrated by formula I may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

The compounds of the present invention have shown inhibition of orexigenic effects, and are thus useful as appetite suppressants either as a single therapy or in conjunction with exercise and other effective appetite suppressing or weight loss medications.

PREFERRED EMBODIMENTS OF THE INVENTION

A compound of formula I preferably exists as the free base or a pharmaceutically acceptable salt. More preferred is the hydrochloride salt, the bisulfate salt, mesylate or the oxalic acid salt of the compound of formula I.

For the Groups $R^1$ and $R^2$

Preferred $R^1$ and $R^2$ groups are independently selected from the group consisting of hydrogen, methyl, ethyl, propyl, pentyl, and isopropyl. Also preferred are $R^1$ and $R^2$ groups independently selected from the group consisting of methyl, ethyl, propyl, isopropyl, phenyl,

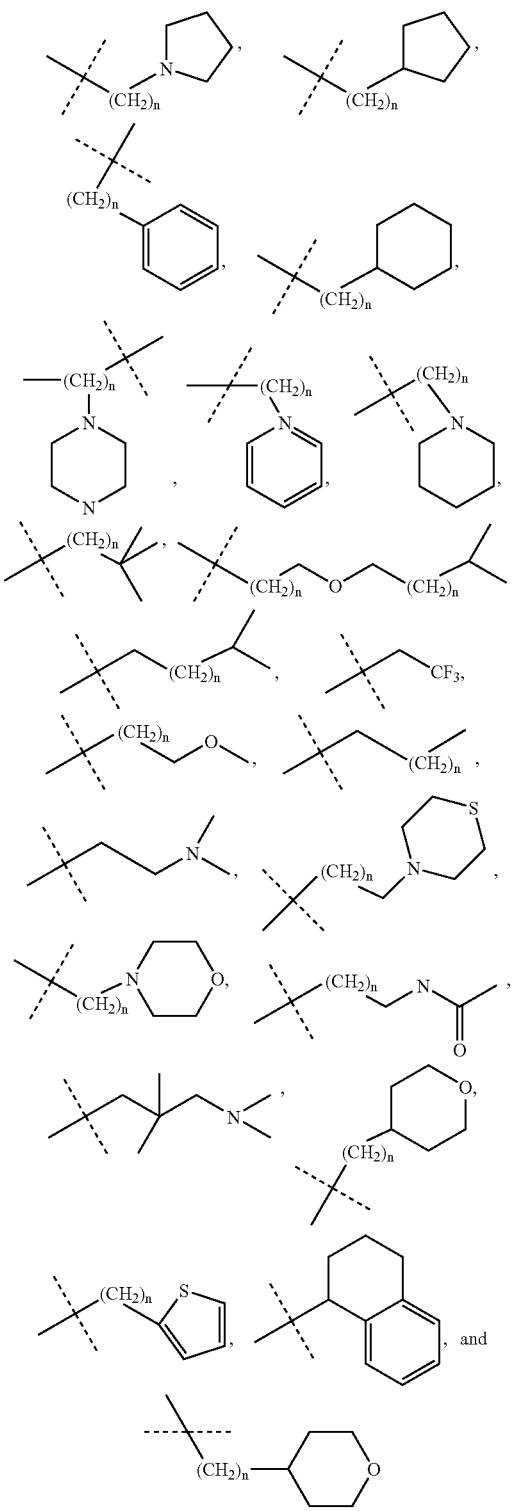

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle or tricycle.

Also preferred are $R^1$ and $R^2$ groups that combine with each other to form a group selected from the group consisting of

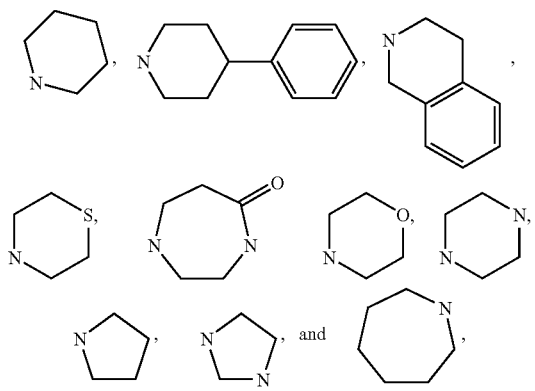

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkylheterocycle.

Preferred $R^3$ and $R^{3'}$ Groups

A preferred $R^3$ is hydrogen. A preferred $R^{3'}$ group is selected from hydrogen, methyl, ethyl, propyl, isopropyl, butyl, isobutyl, phenyl and benzyl. More preferably, both $R^3$ and $R^{3'}$ are hydrogen.

Preferred $R^4$ Groups

A preferred $R^4$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, C1-C5 alkylcycloalkyl, and $C_1$-$C_5$ thioalkyl. More preferred is a $R^4$ group selected from the group consisting of hydrogen, methyl, ethyl, isopropyl, chloro, fluoro, trifluoromethyl, methoxy, ethoxy, thiomethyl, phenyl, and benzyl. Most preferred is an $R^4$ group selected from the group consisting of hydrogen, methyl, ethyl, isopropyl, fluoro, chloro, trifluoromethyl, methoxy, ethoxy, propoxy, isopropoxy, and benzyl.

Though the groups $R^4$ and a $R^5$ may exist as multiple substituents on their respective ring substrates, a preferred embodiment of the invention involves compounds wherein each of $R^4$, and $R^5$ are independently absent, or singly substituted on their respective ring substrates.

Preferred $R^5$ Groups

A preferred $R^5$ group is selected from the group consisting of hydrogen, halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, $C_1$-$C_5$ alkylcycloalkyl, and $C_1$-$C_5$ thioalkyl. More preferred is an $R^5$ group selected from the group consisting of hydrogen, methyl, ethyl, isopropyl, chloro, fluoro, trifluoromethyl, methoxy, ethoxy, thiomethyl, phenyl, and benzyl. A most preferred $R^5$ group is selected from the group consisting of hydrogen, methyl, ethyl, isopropyl, fluoro, chloro, trifluoromethyl, methoxy, ethoxy, trifluoromethoxy, and benzyl.

Preferred $R^6$ and $R^7$ Groups

Preferred are $R^6$ and $R^7$ groups independently selected from the group consisting of hydrogen, methyl, ethyl, propyl, pentyl, isopropyl, phenyl and benzyl.

Also preferred are compounds of formula I wherein $R^6$ and $R^7$ independently combine with each other, and with the nitrogen atom to which they are attached to form a 4, 5, 6, or 7-membered nitrogen containing heterocycle which nitrogen containing heterocycle optionally has substituents selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, $C(O)C_1$-$C_8$ alkyl, $CO(O)C_1$-$C_8$ alkyl, hydroxy, $C_1$-$C_8$ alkoxy, halo, and haloalkyl. Most preferred are compounds of the invention wherein $R^6$ and $R^7$ are both hydrogen.

Preferred Values for n, m, and p, j, k, y, z

A preferred value for n is 0, 1 or 2.
A preferred value for m is 1 or 2.
A preferred value for p is 0, 1, or 2. More preferred is p=1.
A preferred value for j is 1
A preferred value for k is 1
A preferred value for y is 0, or 1
A preferred value for z is 0, or 1.

A preferred compound according to the present invention is a compound selected from the group consisting of:
3-{4-[(3-Methyl-butylamino)-methyl]-phenoxymethyl}-benzamide,
4-{4-[(3-Methyl-butylamino)-methyl]-phenoxymethyl}-benzamide,
4-{3-[(3-Methyl-butylamino)-methyl]-benzyloxy}-benzamide,
4-{4-[(3-Methyl-butylamino)-methyl]-benzyloxy}-benzamide,
4-(2-{4-[(3-Methyl-butylamino)-methyl]-phenoxy}-ethyl)-benzamide,
2-{4-[(3-Methyl-butylamino)-methyl]-phenoxymethyl}-benzamide,
3-{3-[(3-Methyl-butylamino)-methyl]-phenoxymethyl}-benzamide,
3-(4-{[(Methyl-(3-methyl-butyl)-amino]-methyl}-phenoxymethyl)-benzamide,
3-{4-[(3,3-Dimethyl-butylamino)-methyl]-phenoxymethyl}-benzamide,
3-(4-{[2-(Tetrahydro-pyran-4-yl)-ethylamino]-methyl}-phenoxymethyl)-benzamide,
3-(4-{[2-(4-Fluoro-phenyl)-ethylamino]-methyl}-phenoxymethyl)-benzamide,
3-{3-[(3-Methyl-butylamino)-methyl]-benzyloxy}-benzamide,
3-{4-[(3-Methyl-butylamino)-methyl]-benzyloxy}-benzamide,
4-{3-[2-(3-Methyl-butylamino)-ethyl]-benzyloxy}-benzamide,
3-[4-(2-Benzylamino-ethyl)-Phenoxymethyl]-benzamide,
or a pharmaceutically acceptable salt, solvate, enantiomer, diastereomer and diastereomeric mixture thereof.

Preparing Compounds of the Invention

Compounds of formula I may be prepared as described in the following schemes and/or examples or following a combination of schemes know to one of skill in the art for making fragments and combinations thereof. Compounds employed as initial starting materials in the synthesis of compounds of the invention are well known and, to the extent not commercially available, are readily synthesized using specific references provided, or by standard procedures commonly employed by those of ordinary skill in the art and/or found in general reference texts.

More particularly, the compounds of the invention are produced in accordance with schemes 1 through 3 that are described in detail below, or analogous methods thereto. These reactions are often carried out following known procedures, methods, or analogous methods thereto. Examples of such known procedures and/or methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Compounds of formula I wherein k is equal 1 and j equal 0 may be prepared as shown for example in Scheme 1.

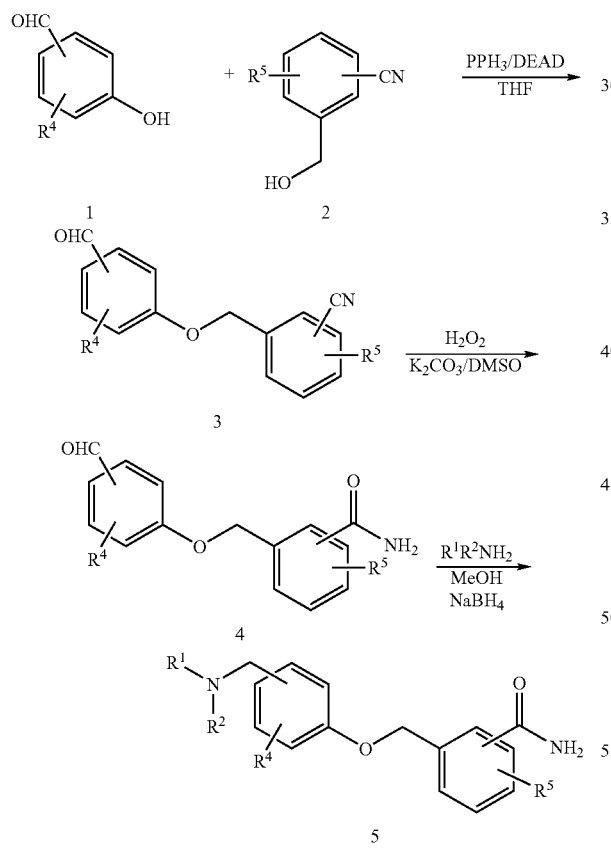

Optionally substituted 4-hydroxy benzaldehyde 1 is reacted with optionally substituted hydroxymethyl benzonitrile 2. The resulting nitrile compound 3 is then converted to the carboxamide 4 by hydrolysis procedures known to one of skill in the art, including for example, the use of hydrogen peroxide and potassium carbonate in a suitable solvent such as DMSO. The resulting amide compound 4 is reductively animated at the aldehyde with an optionally substituted amine (primary and secondary) in a suitable solvent such as methanol and a reducing agent such as for example, sodium cyanoborohydride. The reductive amination of compound 4 results in the compound of formula 5, which is a compound of the invention.

Compounds of formula I wherein j is 1 and k is 0 may be prepared as shown in scheme 2.

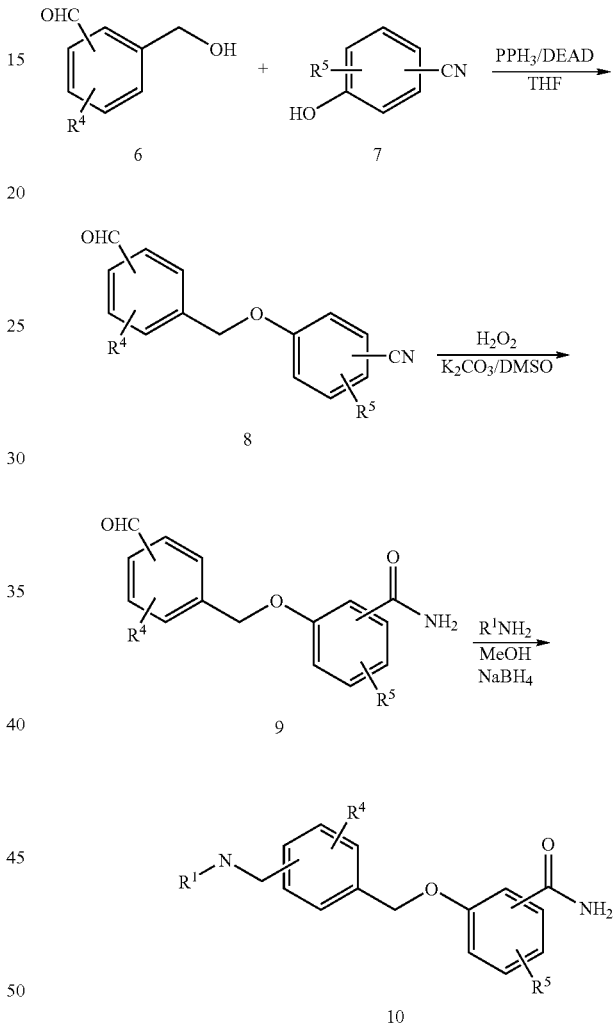

According to scheme 2, hydroxymethyl benzaldehydes (6) is coupled to an optionally substituted hydroxy-benzonitrile (7). The reaction is preferably effected by using Mitsunobu type reaction (triphenylphosphine and ligand (DEAD) in polar aprotic solvents such as THF to afford the coupled product 8. The nitrile group of 8 is hydrolyzed under basic conditions as described previously to afford the carboxamide 9, The carboxamide 9 is then reductively animated to afford the desired amine 10, a compound of formula I. The starting material aldehyde 6 may prepared by hydride reduction (DIBAL reduction) of the corresponding optionally substituted hydroxymethylbenzonitrile in toluene at temperatures of about −15 to 15° C.

Alternatively, compound 5 is utilized to afford a disubstituted compound of the invention as shown in Scheme 3 below.

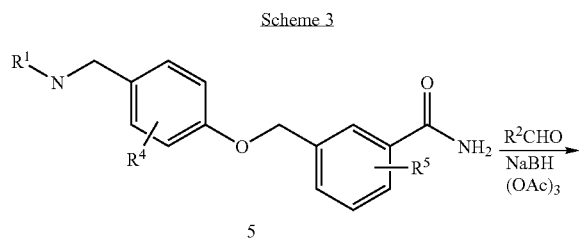

As shown in Scheme 3, compound 5 upon reductive amination affords the amine 11 (wherein neither $R^1$ nor $R^2$ is hydrogen).

Compounds of formula I wherein k is greater than 1, may be prepared for example, according to scheme 4 below:

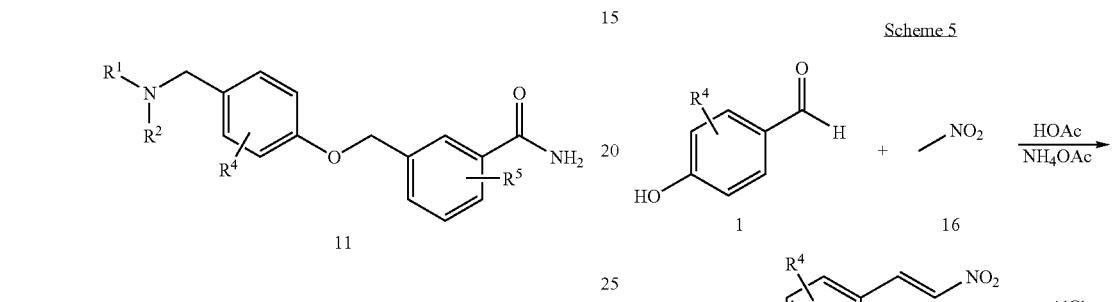

As shown in scheme 4, the use of a substituted hydroxybenzaldehyde affords the ether compound 13 when reacted with a hydroxyethyl benzonitrile. The reaction is carried out using triphenylphosphine, DEAD and THF as solvent. The cyano group of the compound 13 is hydrolyzed under basic conditions using $H_2O_2$ and potassium carbonate, and DMSO as solvent to afford the carboxamide 14. Compound 14 is then reductively animated with a suitable amine to afford the desired compound 15.

Certain compounds of the invention may also be accessed by protocols such as Scheme 5.

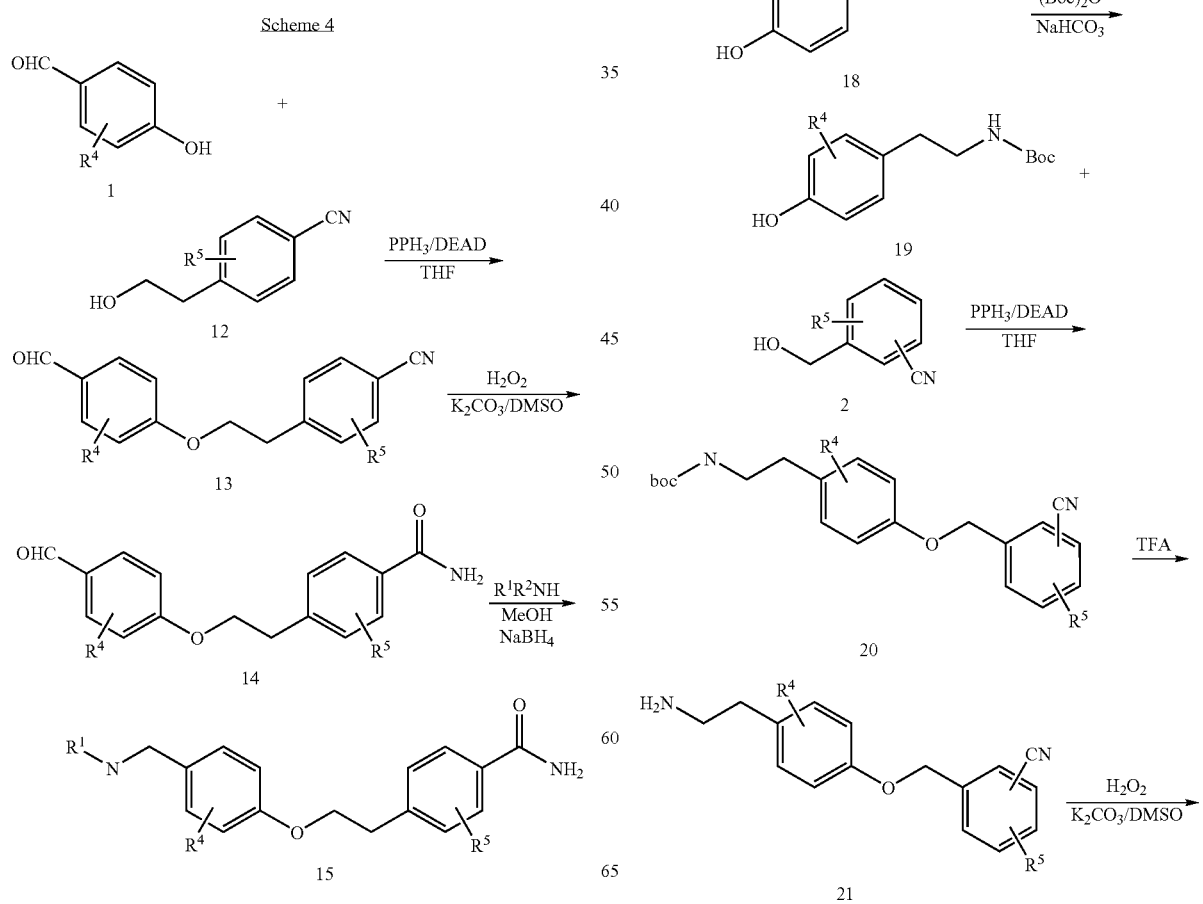

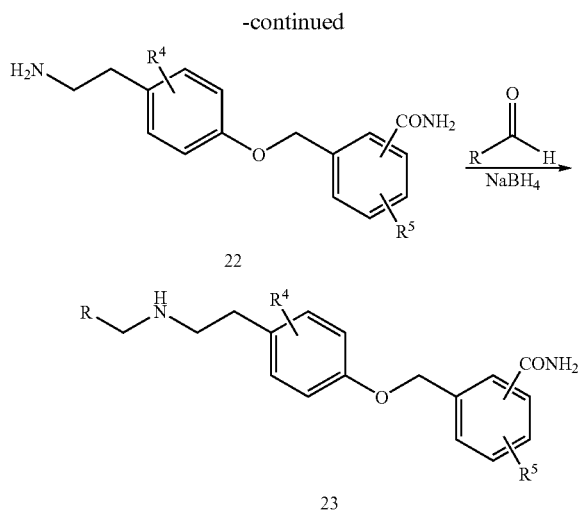

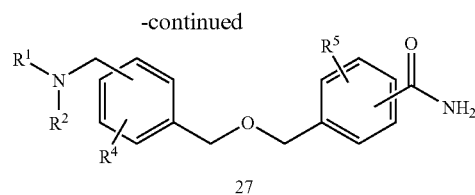

For example, compounds of formula I having p greater than 1, may be more readily accessed by a Michael addition of nitromethane on an aldehyde 1 as shown in Scheme 5. The resulting nitroalkene 17 is reduced to the amine 18, and optionally protected for example by use of a Boc-group as the compound 19. The protected amino compound 19 is then reacted with an appropriately substituted hydroxymethyl-benzonitrile to afford the intermediate 20 which is then deprotected at the Boc group to afford the compound 21. The compound 21 upon hydrolysis of the cyano group to the carboxamide 22 followed by reductive amination affords the desired product 23.

Compounds of formula I wherein k is 1 and j is 1 may be prepared as shown for example in the following Scheme 6.

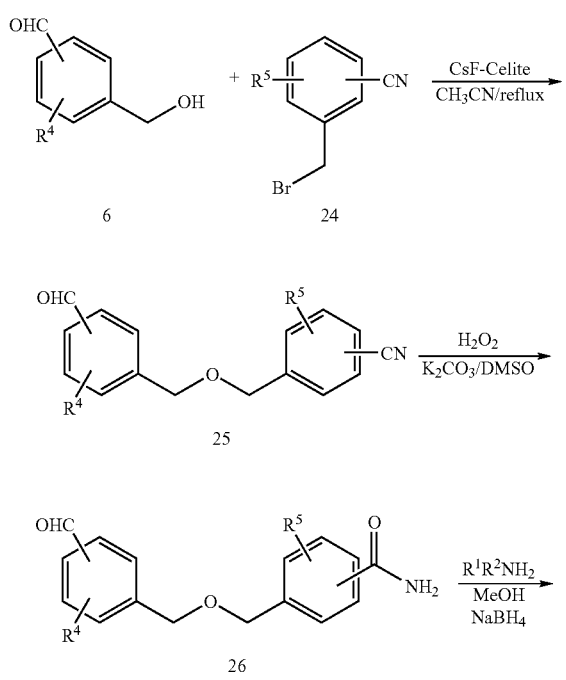

According to scheme 6, an optionally substituted hydroxymethyl benzaldehyde (6) is reacted with optionally substituted cyanobenzyl bromide (24) using cesium fluoride absorbed in Celite, and using acetonitrile as solvent. The reaction mixture is preferably heated to about reflux temperature to afford the coupled compound 25. The nitrile group of 25 is hydrolyzed under basic conditions as described previously to afford product 26. Compound 26 is then reductively animated with a suitable amine to afford the desired compound 27.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in a mammal comprising administering to said mammal a receptor blocking dose of a compound of formula I.

The term "receptor blocking dose", as used herein, means an amount of a compound of formula I necessary to block a mu, kappa, or delta receptor or receptor combination (heterodimer) thereof following administration to a mammal requiring blocking of a mu, kappa, or delta receptor or receptor combination (heterodimer) thereof.

The compounds of formula I or combinations thereof, are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, response of the individual patient, the severity of the patient's symptoms, and the chosen route of administration. Therefore, the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat disorders associated with these receptors or combinations thereof such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptors or receptor combinations (heterodimer) thereof.

Assay Methodology

The compounds of the present invention have been found to display significant activity in an opioid receptor binding assay which measures the ability of the compounds to block the mu, kappa, delta or receptor combination (heterodimer) thereof. The functional antagonist potency (Kb) of the sample compounds was determined using the GTPγS binding assay. GTPgS-based functional assays provide an in vitro measure of the activity of opioid agonists and antagonists. Opioid reference compounds or test compound are incubated with membrane homogenate from cells expressing the cloned human mu, kappa or delta opioid receptor and radiolabeled [35S]GTPgS. If the compound activates the opioid receptor, an increase in the binding of radiolabeled GTPgS is observed. Similarly, if the compound exhibits antagonist activity, it interferes with the ability of the control agonist to stimulate GTPgS binding. These tests provide an in vitro measurement of the activity of the compound at human opioid receptors.

GTP-γ-S Binding Assay

An SPA-based GTP-γ-S assay format was developed based on previous opioid (Emmerson et al., J. Pharm Exp Ther 278, 1121, 1996; Horng et al., Society for Neuroscience Abstracts, 434.6, 2000) and muscarinic (DeLapp et al., JPET 289, 946, 1999) assay formats. Membranes were resuspended in 20 mM HEPES, 100 mM NaCl, 5 mM $MgCl_2$, 1 mM DTT, and 1 mM EDTA. Fifty (50) mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For antagonist assays, specific agonists were added at the following concentrations: (MOR) DAMGO 1 micromolar, (DOR) DPDPE 30 nM, (KOR) U69593 300 nM. Kb's were determined by Cheng-Prusoff equation (see Cheng and Prusoff, Biochem. Pharmacol. 22, 3099, 1973). Results obtained for a sample of compounds of the invention in the GTP-γ-S Binding Assay are shown in table 1 below.

TABLE 1

| Example # | Kb (nM) mu | Kb (nM) kappa | Kb (nM) delta |
|---|---|---|---|
| 1 | >21 | | >41 |
| 2 | 62.86 | | 336.65 |
| 3 | 13.56 | 14.04 | 194.00 |
| 4 | >23 | | >67 |
| 5 | >23 | | >67 |

Formulation

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active Ingredient). As such, the present invention also provides pharmaceutical formulations comprising a compound of the invention and a pharmaceutically acceptable carrier, diluent or excipient therefore.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, the Active Ingredient, a compound of this invention, may be admixed with carriers and diluents and molded into tablets or enclosed in gelatin capsules.

The compositions are preferably formulated in a unit dosage form, each dosage containing from about 1 to about 500 mg, more usually about 5 to about 306 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as Active Ingredient any of the compounds of the present invention.

Formulation 1

Hard gelatin capsules are prepared using the following ingredients:

| Compound | Amount per capsule (mg) | Concentration by weight (%) |
|---|---|---|
| Active Ingredient | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
|---|---|---|
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
|---|---|---|
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
|---|---|---|
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders, which are then passed through a No. 14 mesh U.S. sieve. The granule so produced is dried at 50-60° C. and passed through a No. 18 mesh U.S. sieve. The sodium carboxymethyl starch, magnesium stearate and talc, previously passed through a No. 60 mesh U.S. sieve, are then added to the granules, which after mixing, is compressed on a tablet machine to yield a tablet weighing 100 mg.

Formulation 5

A tablet formula may be prepared using the ingredients below:

| Compound | Amount per capsule (mg) | Percent by weight (%) |
|---|---|---|
| Active Ingredient | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 ml dose are made as follows:

| Compound | Amount per 5 mL suspension (ml) |
|---|---|
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
|---|---|
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

EXAMPLES

Example 1

3-{4-[(3-Methyl-butylamino)-methyl]-phenoxymethyl}-benzamide

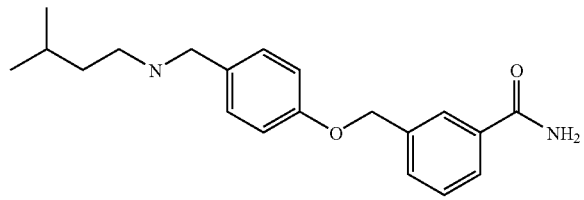

Step 1

3-(4-Formyl-phenoxymethyl)-benzonitrile

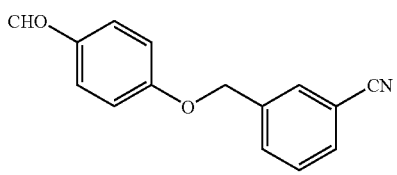

To a solution of 3-(Hydroxymethyl)benzonitrile (1.1 equiv), triphenylphosphine (1.1 equiv), and 4-Hydroxybenzaldehyde (1 equiv) in dry THF was added dropwise Diethyl azodicarboxilate (DEAD) (1.4 equiv). The reaction mixture stirred at room temperature overnight. The reaction was monitored by TLC. The solvent was removed under vacuum. It was purified by silica gel chromatography using Hexane:Ethyl acetate (3:1) to afford the title compound as a white solid.

58% Yield $^1$H NMR (CDCl$_3$, 300 MHz) δ: 9.91 (s, 1H), 7.87 (d, J=9.0 Hz, 2H), 7.69 (s, 1H), 7.68-7.63 (m, 2H), 7.54 (d, J=7.8 Hz, 1H), 7.07 (d, J=8.7 Hz, 2H), 5.17 (s, 2H).

Step 2

3-(4-Formyl-phenoxymethyl)-benzamide

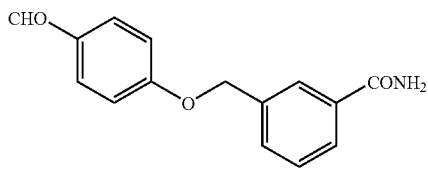

To a solution of 3-(4-Formyl-phenoxymethyl)benzonitrile (1 equiv), in DMSO was added potassium carbonate (0.5 equiv), and hydrogen peroxide (4 equiv). The reaction mixture stirred at room temperature for 2 hours. The reaction was monitored by TLC. It was poured on water and extracted with ethyl acetate (×3). The organic phase was dried over magnesium sulphate, filtered and concentrated under vacuum to yield a white solid.

99% Yield $^1$H NMR (CDCl$_3$, 300 MHz) δ: 9.84 (s, 1H), 7.99-7.98 (m, 1H), 7.88 (d, J=9.0 Hz, 2H), 7.86-7.83 (m, 1H), 7.64 (m, 1H), 7.50 (m, 1H), 7.18 (d, J=8.4 Hz, 2H), 5.17 (s, 2H).

MS (Electrospray): (M$^+$−1) 254.3

Step 3

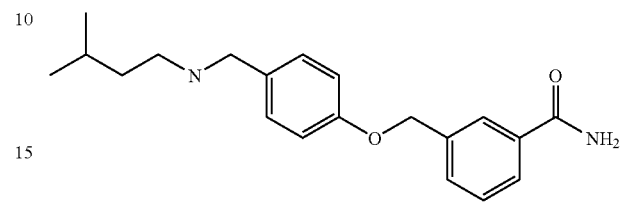

A mixture of 3-(4-formyl-phenoxymethyl)-benzamide (1 equiv), isoamylamine (1 equiv), 4 Å molecular sieves (1000% weight) in methanol (0.1 M) was stirred overnight under nitrogen atmosphere at room temperature. The following day NaBH$_4$ (5 equiv) was added and the reaction mixture was stirred for 3 hours. The reaction can be monitored by TLC analysis. The reaction mixture was filtered off and the solvent evaporated to yield a residue which was purified by silica gel chromatography using CHCl$_3$:EtOH 7%: NH$_4$OH 0.7 to afford the title compound as a solid.

75% Yield $^1$H NMR (CD$_3$OD, 300 MHz) δ: 7.96 (s, 1H), 7.82-7.80 (m, 1H), 7.64-7.61 (m, 1H), 7.49-7.46 (m, 1H), 7.25 (d, J=8.7 Hz, 2H), 6.97 (d, J=9.0 Hz, 2H), 5.13 (s, 2H), 3.69 (s, 2H), 2.61-2.56 (m, 2H), 1.61-1.54 (m, 1H), 1.45-1.40 (m, 2H), 0.89 (d, J=6.6 Hz, 6H).

MS (Electrospray): (M$^+$+1) 327.3

Example 2

4-{4-[(3-Methyl-butylamino)-methyl]-phenoxymethyl}-benzamide

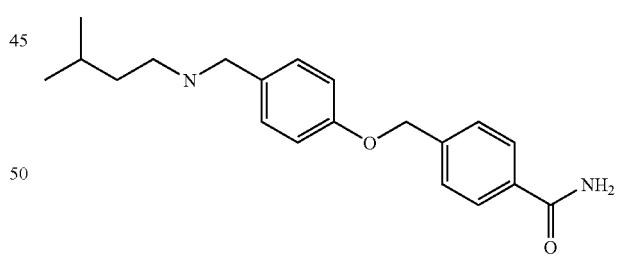

The compound of Example 2 may be prepared essentially as described in Example 1.

42% Yield $^1$H NMR (CD$_3$OD, 300 MHz) δ: 7.87 (d, J=8.4 Hz, 2H), 7.52 (d, J=8.7 Hz, 2H), 7.24 (d, J=8.7 Hz, 2H), 6.95 (d, J=8.7 Hz, 2H), 5.14 (s, 2H), 3.66 (s, 2H), 2.58-2.53 (m, 2H), 1.58-1.56 (m, 1H), 1.43-1.36 (m, 2H), 0.88 (d, J=6.6 Hz, 6H).

MS (Electrospray): (M$^+$+1) 327.3

HPLC=98% @ 5.95 m (5/95 to 95/5 ACN/(0.1% TFA in water) over 10 minutes, Zorbax SB-Phenyl 4.6 mm×15 cm×5 micron, λ=254 nM.de

Example 3

4-{3-[(3-Methyl-butylamino)-methyl]-benzyloxy}-benzamide

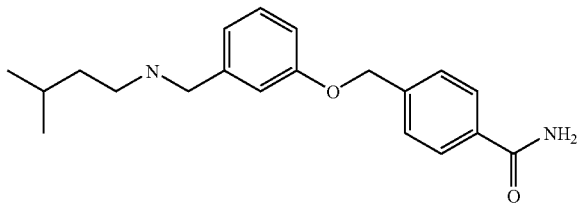

The compound of Example 3 may be prepared essentially as described in Example 1.

32% Yield $^1$H NMR (CD$_3$OD, 300 MHz) δ: 7.83 (d, J=8.7 Hz, 2H), 7.43 (s, 1H), 7.36-7.34 (m, 2H), 7.34-7.30 (m, 1H), 7.04 (d, J=9.0 Hz, 2H), 5.15 (s, 2H), 3.76 (s, 2H), 2.59-2.56 (m, 2H), 1.60-1.55 (m, 1H), 1.44-1.40 (m, 2H), 0.92 (d, J=6.6 Hz, 6H).

MS (Electrospray): (M$^+$+1) 327.2

HPLC=94% @ 5.96 m (5/95 to 95/5 ACN/(0.1% TFA in water) over 10 minutes, Zorbax SB-Phenyl 4.6 mm×15 cm×5 micron, λ=254 nM.de

Example 4

4-{4-[(3-Methyl-butylamino)-methyl]-benzyloxy}-benzamide

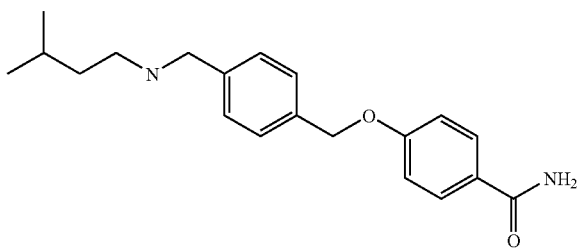

The compound of Example 4 may be prepared essentially as described in Example 1.

59% Yield $^1$H NMR (CD$_3$OD, 300 MHz) δ: 7.85 (d, J=8.4 Hz, 2H), 7.42-7.38 (m, 4H), 7.04 (d, J=8.7 Hz, 2H), 5.15 (s, 2H), 3.79 (s, 2H), 2.58-2.53 (m, 2H), 1.65-1.58 (m, 1H), 1.46-1.40 (m, 2H), 0.90 (d, J=6.6 Hz, 6H).

MS (Electrospray): (M$^+$+1) 327.2

HPLC=97% @ 6.02 m (5/95 to 95/5 ACN/(0.1% TFA in water) over 10 minutes, Zorbax SB-Phenyl 4.6 mm×15 cm×5 micron, λ=254 nM.de

Example 5

4-(2-{4-[(3-Methyl-butylamino)-methyl]-phenoxy}-ethyl)-benzamide

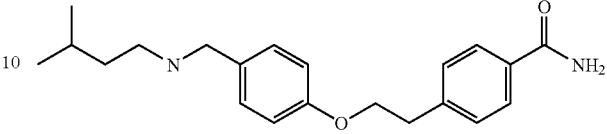

The compound of Example 5 may be prepared essentially as described in Example 1.

71% Yield $^1$H NMR (CD$_3$OD, 300 MHz) δ: 7.81 (d, J=8.1 Hz, 2H), 7.40 (d, J=8.1 Hz, 2H), 7.23 (d, J=8.7 Hz, 2H), 6.87 (d, J=8.7 Hz, 2H), 5.15 (s, 2H), 4.21 (t, J=6.6 Hz, 2H), 3.70 (s, 2H), 3.12 (t, J=6.6 Hz, 2H), 2.63-2.58 (m, 2H), 1.65-1.58 (m, 1H), 1.45-1.40 (m, 2H), 0.89 (d, J=6.6 Hz, 6H).

MS (Electrospray): (M$^+$+1) 341.3 (M$^+$−1) 339.4

HPLC=91% @ 6.07 m (5/95 to 95/5 ACN/(0.1% TFA in water) over 10 minutes, Zorbax SB-Phenyl 4.6 mm×15 cm×5 micron, λ=254 nM.de

We claim:

1. A compound selected from the group consisting of:
   3-{4-[(3-Methyl-butylamino)-methyl]-phenoxymethyl}-benzamide,
   4-{4-[(3-Methyl-butylamino)-methyl]-phenoxymethyl}-benzamide,
   4-{3-[(3-Methyl-butylamino)-methyl]-benzyloxy}-benzamide,
   4-{4-[(3-Methyl-butylamino)-methyl]-benzyloxy}-benzamide,
   4-(2-{4-[(3-Methyl-butylamino)-methyl]-phenoxy}-ethyl)-benzamide,
   2-{4-[(3-Methyl-butylamino)-methyl]-phenoxymethyl}-benzamide,
   3-{3-[(3-Methyl-butylamino)-methyl]-phenoxymethyl}-benzamide,
   3-(4-{[Methyl-(3-methyl-butyl)-amino]-methyl}-phenoxymethyl)-benzamide,
   3-{4-[(3 ,3-Dimethyl-butylamino)-methyl]-phenoxymethyl}-benzamide,
   3-(4-{[2-(Tetrahydro-pyran-4-yl)-ethylamino]-methyl}-phenoxymethyl)-benzamide,
   3-(4-{[2-(4-Fluoro-phenyl)-ethylamino]-methyl}-phenoxymethyl)-benzamide,
   3-{3-[(3-Methyl-butylamino)-methyl]-benzyloxy}-benzamide,
   3-{4-[(3-Methyl-butylamino)-methyl]-benzyloxy}-benzamide,
   4-{3-[2-(3-Methyl-butylamino)-ethyl]-benzyloxy}-benzamide,
   3-[4-(2-Benzylamino-ethyl)-Phenoxymethyl]-benzamide, or a pharmaceutically acceptable salt thereof.

2. A pharmaceutical composition comprising a compound of claim 1 in association with a carrier, diluent and/or excipient.

3. A compound of claim 1 which is
3-{4-[(3-Methyl-butylamino)-methyl]-phenoxymethyl}-benzamide,
4-{4-[(3-Methyl-butylamino)-methyl]-phenoxymethyl}-benzamide,
4-{3-[(3-Methyl-butylamino)-methyl]-benzyloxy}-benzamide,
4-{4-[(3-Methyl-butylamino)-methyl]-benzyloxy}-benzamide,
4-(2-{4-[(3-Methyl-butylamino)-methyl]-phenoxy}-ethyl)-benzamide, or a pharmaceutically acceptable salt thereof.

* * * * *

UNITED STATES PATENT AND TRADEMARK OFFICE
CERTIFICATE OF CORRECTION

PATENT NO. : 7,381,750 B2
APPLICATION NO. : 10/598696
DATED : June 3, 2008
INVENTOR(S) : Marta Garcia De La Torre It is certified that error appears in the above-identified patent and that said Letters Patent is hereby corrected as shown below:

On the Title page:
Insert --(60) Related U.S. Application Data
Provisional application no. 60/553,184, filed March 15, 2004--

Col. 1, line 3 of the specification, insert the following cross-reference after the title:
--This application is the national phase application, under 35 USC 371, for PCT/US2005/007051, filed March 8, 2005, which claims the benefit, under 35 USC 119(e), of EP application 04380058.0, filed March 12, 2004, and US provisional application 60/553,184, filed March 15, 2004.--

Signed and Sealed this

Thirtieth Day of November, 2010

David J. Kappos
*Director of the United States Patent and Trademark Office*